United States Patent [19]

Howard, Jr. et al.

[11] Patent Number: 5,064,755

[45] Date of Patent: Nov. 12, 1991

[54] TWO-SITE CONFIRMATORY ASSAY

[75] Inventors: Lawrence V. Howard, Jr., Libertyville; MaryCaren Craine, Grayslake, both of Ill.

[73] Assignee: Abott Laboratories, Abbott Park, Ill.

[21] Appl. No.: 228,363

[22] Filed: Aug. 4, 1988

[51] Int. Cl.$^5$ .................. G01N 33/53; G01N 33/566; C12Q 1/02; C12Q 1/04
[52] U.S. Cl. ........................................ 435/7.36; 435/4; 435/7.1; 435/7.2; 435/7.9; 435/29; 435/34; 436/501; 436/510; 436/536; 436/537; 436/538
[58] Field of Search ............... 436/518, 510, 823, 537, 436/548, 501, 536, 538; 435/7, 4, 34, 7.36

[56] References Cited

U.S. PATENT DOCUMENTS

| | | |
|---|---|---|
| 3,935,074 | 1/1976 | Rubenstein et al. |
| 4,683,196 | 7/1987 | McLaughlin |
| 4,737,456 | 4/1988 | Weng et al. |
| 4,818,688 | 4/1989 | Adamich et al. ................ 435/7 |

OTHER PUBLICATIONS

Pediatric Research, vol. 21, No. 4, Abs. No. 1453, Apr. 1987.
Hammerschlag, M. R., 1988, Pediatr. Infect. Dis. J., False Positive Results with the Use of Chlamydial Detection Tests the Evaluation . . . , vol. 7, 11-14 (Jan. 1988), Abstract.
Howard et al. 1986. Evaluation of Chlamydiazyme for the Detection of Genital Infections Caused by Chlamydia Trachomatis J. Clin. Microbiol. 23 329.
Ausria Auszyme HB$_s$Ag Confirmatory Assay Package Insert, Jul. 1985.
Chlamydiazyme Package Insert, Jul. 1987.
Neonatal Infectious Diseases Abstract No. 1453, Apr. 1987.
Nurminen, Marjatta et al., "The Genus-Specific Antigen of Chlamydia: Resemblance to the Lipopolysaccharide of Enteric Bacteria", Science; 220:1279-1281, June 17, 1983.
Caldwell, Harlan D. et al. "Monoclonal Antibody Against a Genus-Specific Antigen of Chlamydia Species: Location of the Epitope on Chlamydial Lipopolysaccharide", *Infection and Immunity*, 44(2):306-314, May, 1984.
Thornley, Margaret J. et al., "Properties of Monoclonal Antibodies to the Genus-Specific Antigen of Chlamydia and Their Use for Antigen Detection by Reverse Passive Haemagglutination"; *Journal of General Microbiology*, 131:7-15 (1985).
Numinen, Marjatta et al., "Chemical Characterization of Chlamydia Trachomatis Lipopolysaccharide", *Infection and Immunity*, 48(2):573-575, May, 1985.
Brade, Lore et al., "Antigeic Properties of Chlamydia Trachomatis Lipopolysaccharide", *Infection and Immunity*, 48(2):569-572, May, 1985.
Brade, Helmut et al., "Chemical and Serological Investigates on the Genus-Specific Lipopolysaccharide Epitope of Chlamydia", *Proc. Natl. Acad. Sci. U.S.A.*, 84:2508-2512, Apr., 1987.
Kallestad Technical Bulletin, Pathfinder Chlamydia EIA Blocking Assay Procedure, dated 04-19-88.

*Primary Examiner*—Esther L. Kepplinger
*Assistant Examiner*—Janelle Graeter
*Attorney, Agent, or Firm*—Thomas D. Brainard

[57] ABSTRACT

In an assay where a ligand or organism is detected by a detector binding protein ("DBP") capable of generating a signal in proportion to the amount of ligand or organism bound to the DBP, the presence of the ligand or organism is confirmed by the use, prior to or concurrently with the DBP, of a confirmatory binding protein ("CBP") which binds to a second site on the ligand or organism, and thereby prevents the DBP from binding to the first site. Thus, a reduction in signal of a predetermined amount indicates the true presence of the ligand or organism, while failure to obtain signal reduction of a predetermined amount indicates that the original signal was a false positive due to assay artifact or detection of related ligands or organisms. In a preferred embodiment, the CBP is a monoclonal antibody and the organism is derived from Chlamydia species.

15 Claims, No Drawings

TWO-SITE CONFIRMATORY ASSAY

BACKGROUND OF THE INVENTION

This invention relates to confirmatory assays and, in particular, to a novel confirmatory assay in which true positives are distinguished from false positives caused by related ligands or cross-reactive organisms, as well as false positives caused by non-specific assay artifacts.

Confirmatory assays are well known in the art and generally involve repeating with some modifications an initial assay which has detected the presence of a ligand, antigen or organism in a test sample. Known confirmatory assays use confirmatory binding proteins (CBPs), usually antibodies, which have specificities identical to the detector binding protein (DBP) of the detecting assay but which are unable to generate a signal. By addition of the CBP prior to the DBP, the binding sites normally occupied by the DBP are blocked and the signal is correspondingly reduced. For example, a commercially available (from Abbott Laboratories, Abbott Park, IL.) assay for confirming the presence of Hepatitis B Surface Antigen ($HB_sAg$) utilizes human anti $HB_sAg$ as a CBP to block available sites on antigen in the sample. Then the assay is repeated, and a signal reduction of 50% confirms the presence of $HB_sAg$.

These assays eliminate extraneous signal generation caused by non-specific binding of the DBP to various assay components to give false positive signals. Such false positive signals caused by DBP binding to (i.e. detection of) assay components are referred to herein as "assay artifact" signals.

In contrast, false positive signals may also be generated by DBP binding to ligands or organisms which closely resemble the target ligand or organism, or are cross-reactive therewith. Due to identical specificity between the DBP and the CBP, conventional confirmatory assays can eliminate assay artifact false positives, but not false positives originating from closely related or cross reactive ligands or organisms in the test sample. This disadvantage is overcome by the present invention.

SUMMARY OF THE PRESENT INVENTION

The present invention comprises a confirmatory assay which confirms the presence in a sample of a ligand or organism that has previously been detected by a detector binding agent or protein (DBP) binding to a first site on the ligand or organism to generate a measurable signal. A novel confirmatory binding agent or protein (CBP), having a specificity distinct from that of the DBP, is used prior to or concurrently with the addition of a DBP. The CBP binds to a second site on the ligand or organism, thereby to prevent binding of the DBP to the first site and to cause a reduced signal. As long as the CBP can differentiate the target ligand or organism from closely related ligands or organisms, the present confirmatory assay can discern true positive signals from both types of false positive signals: those arising from assay artifact as well as those arising from closely related ligands and organisms.

In another aspect, the present invention comprises a method of confirming the presence of a ligand or organism in a test sample previously tested as positive. The method comprises contacting the test sample, prior to or concurrently with the DBP, with the CBP which binds to a second site on the ligand or organism. Preferably, the second site is shared by neither related ligands or organisms nor assay components. The DBP is prevented from binding to first sites on the target ligand or organism (due to the prior or competing presence of the CBP) but is able to bind to similar sites on closely related ligands or organisms and bind non-specifically to various assay components. By measuring the amount by which the signal is decreased as a result of the CBP, one can confirm the true presence of the target ligand or organism in the sample, as distinct from assay artifact and related ligands or organisms.

DETAILED DESCRIPTION OF THE INVENTION

The confirmatory assay of the present invention can be used for detecting a number of different analytes. For example, the analyte may comprise a ligand, an antigen, a hapten, a microorganism or components thereof, or other biocomponents. Throughout this specification and claims the terms "ligand" and "analyte" are used interchangeably to designate any of the above listed analytes and their equivalents. The only requirement is that the ligand have at least two binding sites related such that a CBP bound to the second of the sites prevents a DBP from binding to the first site. In other words, the CBP and the DBP are specific for different sites or epitopes.

The DBP may comprise any binding agent capable of binding the first site on the ligand and thereafter generating a signal proportional to the amount of ligand bound to the receptor. Although they are usually proteins, "DBP" as used herein may comprise non-protein or mixed protein-nonprotein binding agents. Typically, the DBP comprises an antibody or labeled antibody capable of detecting and signaling the ligand. The antibody may be monoclonal or polyclonal; the techniques for preparing both are well known in the art and need not be described in detail here. See e.g. Kohler & Milstein, *Nature*, v.256, p.495 (Aug. 7, 1975), The CBP likewise may comprise any binding agent capable of binding a second site on the ligand. Preferably, the CBP comprises an antibody, either polyclonal or monoclonal, although other CBPs, such as biotin, avidin, lectins or protein A, are contemplated as well. It is also possible to use a CBP comprising a combination of the above described receptors. Some specific CBPs are described in the Examples which follow.

It is an important aspect of this invention that the CBP have a specificity which differs from that of the DBP. By this it is meant that the CBP binds to a binding site (usually an antigenic determinant or epitope) on the analyte that is distinct from the binding site to which the DBP binds. In other words, the analyte must be at least divalent having two or more distinct binding regions.

When the CBP binds to the second site it prevents the DBP from binding to the first site. Prevention of binding may be accomplished in a number of ways. For example, the binding sites on the ligand or organism may be adjacent or overlapping. Thus, binding of the CBP to the second site physically blocks the binding of the DBP to the first site. Although it is preferred that the antigenic sites be located in the same vicinity as described above, it is possible and within the scope of this invention that binding of the CBP to the second site alters the tertiary structure of a remote first binding site to prevent its binding of the DBP. As used herein, the term "preventing binding" encompasses physical blocking or steric hindrance and modification of tertiary structure as discussed above, as well as any equivalent preventing means known in the art.

The relevant art is replete with examples of signal generation systems which could be adapted for use with the present invention. By way of example, not limitation, the signal generating system may be color forming compounds, radioactive compounds, fluorescing compounds or electroactive compounds. Preferably, the signal generating system is a color forming compound resulting from the action of an enzyme label conjugated to or otherwise associated with the DBP. The mechanism of such enzyme immunoassays (EIAs) is well known in the art and need not be described in detail here.

It is also well known in the art that false positive signals can arise in EIAs as a result of several factors. Signal can be generated as a result of the interaction of color forming compounds and assay components; as a result of enzyme non-specifically binding to assay components; as a result of non-specific binding of labeled DBP to assay components; and as a result of DBP binding to non target antigens where the antigen has sufficient structural similarity to the target antigen to cause recognition and binding. The first three of these false positive signals are referred to herein as "assay artifact" signals or "assay artifact" false positives. The incidence of these signals is reduced or eliminated by conventional blocking confirmatory assays.

However, the fourth type of false positive, caused by structurally related non-target ligands or antigens, have not been resolvable by confirmatory assays previously known in the art. This latter type of false positive signal is herein called "related ligand" signal or "related ligand" false positives. When the ligand to be detected is an organism or a part thereof, related organism false positive signals are often caused by organisms exhibiting cross-reactivity.

In use, the presence of the target ligand or analyte is confirmed by the assay of the present invention when the signal generated following use of the CBP is reduced by a predetermined amount. An assay is first performed using the DBP to bind the first site of the target ligand to generate a first signal in proportion to the amount of ligand detected. It is always possible, however, that the signal detected is resulting from related ligand false positives and/or assay artifact false positives. To confirm the presence of the target ligand by the present invention, the sample is contacted with a reagent containing the CBP. The CBP binds to the second site on the target ligand but does not bind to related non-target ligands or to the assay components themselves.

Confirmatory receptor bound to the target ligand prevents the binding of the DBP to this ligand. Thus, if the signal generated is reduced by a predetermined amount, it is because the signal originally given resulted primarily from true target ligand and not from related ligand false positives or assay artifact false positives. Conversely, if the signal generated upon confirmation is not reduced by a predetermined amount, then the signal given initially was a false positive resulting from either closely related ligand signal or assay artifact signal. Preferably, the predetermined amount by which the signal must be reduced to confirm the presence of the ligand is about 50 percent.

The CBP may be added to the sample prior to or concurrently with the DBP. In the first case, the CBP binds to the second site and occupies it to prevent binding of the DBP to the first site. In the case of concurrent addition of CBP and DBP, it is believed that the two binding proteins compete for their respective sites in much the same way two binding proteins would compete for a common site. Although signal reduction can be expected with prior addition of DBP, the necessity of an extra step in the protocol is disadvantageous. Therefore, concurrent addition of CBP and DBP in a mixed reagent is preferred.

The CBPs of the present invention find particular utility in diagnostic assays. When used prior to or concurrently with a DBP, the CBPs can enhance the specificity of the assay by eliminating cross reactive false positives.

The examples which follow show that multiple CBPs are obtained relatively easily. Successful CBPs were produced in both mouse and rat species; from both LGV and Serotype E strains; and from immunizations according to a plurality of schedules and with both intact cells and a detergent extract of cells. The examples which follow describe particular embodiments of the invention, although the invention is in no way limited by these examples. The scope of the invention is limited only by the appended claims.

EXAMPLE 1

Chlamydiazyme® EIA (Abbott Laboratories, Abbott Park, IL) is a commercially available enzyme-linked immunoassay that detects chlamydial lipopolysaccharide (LPS) directly in human genital specimens. In this experiment, performed according to the package insert, the material collected on a genital swab is eluted into a specimen dilution buffer (SDB) which is added to a treated polystyrene bead. The chlamydial LPS, which is solubilized by the SDB, attaches to the bead. After washing to remove unattached material, rabbit anti-chlamydial LPS antibody is incubated with the bead. The bead is washed and the bound rabbit immunoglobulin (Ig) is reacted with peroxidase:goat anti rabbit Iq conjugate. The bead is washed and attached conjugate is determined by incubation with o-phenylenediamine (OPD) substrate to generate a colored product. Measurable signals are obtained as absorbance of the colored product at 492 nm in a spectrophotometer.

The Chlamydiazyme® EIA has been reported to react with several gram negative bacteria that share a lipopolysaccharide (LPS) epitope with *Chlamydia* species. The confirmatory assay of the present invention can be used to eliminate the false positives that can occur if these cross reactive organisms are present in clinical sample being assayed for *Chlamydia.*

EXAMPLE 2

Production of Mouse Monoclonal Antibody to Chlamydial LPS

*C. trachomatis* strain LGV 434 (ATCC VR902) was propagated in McCoy cells and purified on Renografin density gradients. An extract of purified *Chlamydia* was prepared by incubating $8.0\times10^{10}$ chlamydial cells in 7.5 ml of 0.67% sodium deoxycholate (NaDOC) for 2 hr at 45° C. The suspension was centrifuged at 18,000 $\times$g for 30 min at 35° C. The supernatant fluid was dialyzed against PBS for 3 days. The precipitate which formed was pelleted by centrifugation, resuspended in 5 ml phosphate buffered saline (PBS) and sonicated at full output for 30 seconds in the cup horn of a cell disruptor (Heat Systems Ultrasonics, Inc., Farmingdale, NY) to disperse large aggregates. The preparation was stored at −20° C.

Mouse monoclonal antibodies H-5, H-210, and H35 were obtained by immunization of BALB/c mice with LGV cells or the NaDOC extract prepared above. In each mouse the immunization dose was $1 \times 10^9$ LGV cells or if immunized with the NaDOC extract, the equivalent of $1 \times 10^9$ cells based on reactivity in the Chlamydiazyme ® assay. Subcutaneous (sc) injections were made at two auxiliary and two inguinal sites. A prefusion booster of intact LGV cells was given intravenously (iv) at 2 and 3 days before fusion. The specific immunization regimens are given below.

Spleens were removed and the cells were fused with SP 2/0 cells (ATCC No. CRL1581) as described previously by Goding, J. W. *Monoclonal Antibodies: Principles and Practice*, Academic Press Inc., London, 1983. Supernatant fluids of hybridoma cells were screened in an EIA as follows. LGV strain 434 was incubated in Chlamydiazyme® SDB buffer with beads which were similar to those of a Chlamydiazyme® kit. Hybridoma fluids were tested at a dilution of 1/10 and the bound mouse Ig was detected by incubation with peroxidase-labelled goat anti mouse Ig. Suitable labeled Iq conjugates are commercially available from a number of sources including Chemicon International, Inc., El Segundo, CA, and Kirkegaard and Perry Laboratories, Inc., Gaithersburg, MD. The substrate was o-phenylenediamine (OPD). Hybrids "screened positive" for chlamydial antigen if the OD signal was of an arbitrarily predetermined magnitude.

Positive hybrids were then cloned by limiting dilution. Selected clones were tested for their ability to block DBP reagent in a Chlamydiazyme® assay. Clones successfully "blocked" if a signal reduction of 50% or more was achieved. The success ratio of reproducibility is given for each experiment below. Then, ascites fluid was produced in pristane primed mice by intraperitoneal (ip) injection of approximately $1\times10^7$ hybridoma cells.

Mouse #1: Mab H-5, an IqGl, was obtained by immunization of a mouse with intact LGV mixed with incomplete Freund's adjuvant. This immunogen was injected at the 4 sc sites. Eleven weeks later the mouse was injected ip with the NaDOC extract without adjuvant. Four weeks later the mouse was given prefusion boosts (iv) with intact LGV and the spleen cells were removed and fused. Of 39 wells exhibiting growth, 3 screened positive for chlamydial antigen in the EIA. One of these (H-5) was tested for blocking as a CBP and it was successful. Two other mice immunized according to identical schedules produced 90 hybrids, of which 4 screened positive. These were not tested for blocking.

Mouse #2: Mab H-210, an IqG2b, was obtained by immunization of a mouse at the four sc sites with intact LGV cells mixed with complete Freund's adjuvant. Six weeks later this immunization was repeated with incomplete Freund's adjuvant used in place of the complete adjuvant. Eight weeks later the mouse was given prefusion boosts iv and spleen cells were fused. Of 262 hybrids, 56 screened positive. Six of these were tested for their ability to block and 4 were successful (H-210 being one). Two other mice immunized according to this schedule produced 28 hybrids, none of which screened positive.

Mouse #3: Mab H-35, was obtained by immunization of a mouse at the four sc sites with the LGV mixed with incomplete Freund's adjuvant. Four months later the mouse was immunized ip with LGV. One week before fusion the mouse was given three additional ip injections with LGV. The mouse was given the prefusion iv booster injections and spleen cells were fused 23 weeks after the start of immunization. Of 46 hybrids produced, 1 (H-35) screened positive and was a successful blocker. One other mouse immunized according to this schedule produced 170 hybrids, 16 of which screened positive. Three of the 16 were tested for blocking and two were successful.

EXAMPLE 3

Immunization of Rat with LGV

The clone producing Mab H-98 was derived from a rat that was immunized sc at the four sites with LGV cells mixed with complete Freund's adjuvant. Five weeks later the immunization was repeated except that incomplete adjuvant was used. Three weeks later the rat was given two iv injections of LGV, as described for the mice, and spleen cells were fused as in Example 2. Of 131 hybrids produced, 72 screened positive. Two of these (H-98 being one) were tested for blocking and both were successful.

EXAMPLE 4

Immunization of Mice with Serotype E *Chlamydia*

Mab H-69, an IgG3, was derived from a mouse that was injected with a serotype E of *C. trachomatis* that had been propagated in yolk sac of eggs and purified on Renografin density gradients. The mouse was injected with $2\times10^8$ particles that had been mixed with complete Freund's adjuvant and injected ip and sc at axial and inguinal sites. Four weeks later the immunization was repeated with the same dose mixed with incomplete Freund's adjuvant and injected ip and at six sites sc. Four and eight weeks later mice were boosted iv with $1\times10^8$ cells with each injection. Three days after the last iv injection spleen cells were harvested and fused as in Example 2. Of 115 hybrids produced, 2 screened positive. One of these (H-69) was tested for blocking and was successful.

EXAMPLE 5

A. SPECIFIC RABBIT ANTISERA

Rabbit antisera can be produced which reacts with either the cross-reactive or unique epitope of chlamydial LPS. Brade et al. Antigenic Properties of Chlamydia trachomatis Lipopolysaccharide, *Infect. Immun.* 48: 569–572, (1985). In order to demonstrate the specificity of the rabbit Iq preparations, adsorption experiments were performed. When rabbit Ig that reacts with the cross-reactive LPS epitope, but lacks reactivity with the unique epitope, is adsorbed with *S. minnesota* Re 595, no reactivity to chlamydial LPS should remain. Conversely, rabbit Ig with reactivity with only the unique chlamydial LpS epitope would have no change in reactivity with chlamydial LPS after adsorption with *S. minnesota* Re 595.

The specificity of two rabbit antisera with reactivity against the unique or cross-reactive epitope was demonstrated by incubating $2.6\times10^{10}$ cells of *S. minnesota* with each of the two antisera preparations. The antisera were adsorbed at 0.1 to 1.0 ug per ml of Ig or at a 1/500 dilution of antisera. The antigen and antibody mixtures were incubated for 2 hours at 37° C. and centrifuged at 8,000 ×g for 10 min. The supernatant fluids containing the adsorbed sera were then tested by the routine EIA. Chlamydial LPS was adsorbed to polystyrene beads and the LPS antigen was incubated with the unadsorbed or adsorbed rabbit Iq. The attached rabbit Ig was detected with peroxidase labelled goat anti-rabbit Ig and the color was measured after incubation with OPD substrate. The results are shown in Table 1.

TABLE 1

| OD in EIA Using Rabbit Antisera Against The Cross-reactive or Genus-specific LPS Epitope: Before and After Adsorption with Salmonella Re 595 | | |
|---|---|---|
| Rabbit Antisera | Anti-Crossreactive LPS Epitope | Anti-Genus-Specific LPS Epitope |
| Before adsorption | 0.77 | 0.96 |
| After adsorption | 0.01 | 1.00 |

When the rabbit Iq against the cross-reactive epitope was adsorbed with *S. minnesota* Re 595 the OD in the assay using LGV as antigen decreased from 0.77 to 0.01. On the other hand, when the rabbit Ig directed against the unique epitope was tested, there was no significant change in the OD after adsorption. This demonstrated that the two antisera preparations contained reactivity to different chlamydial LPS epitopes.

B. BLOCKING OF CROSS-REACTIVE EPITOPE

MAb H-5 was tested for the ability to block the reaction of rabbit antibody directed against the cross-reactive epitope of chlamydial LPS. The blocking antibody (MAb H-5) was added to the rabbit antisera solution at various concentrations and an unblocked control was included. The LGV strain was tested at 1.6 ×10$^4$ cells per ml in the routine EIA procedure. At a final concentration of 0.5 ug per ml the MAb H5 blocked the absorbance of the EIA by 60.1% (Table 2).

TABLE 2

| Final Concentration of MAb Added to Rabbit Antibody Solution | Net OD in EIA |
|---|---|
| 10.0 | 0.022 |
| 5.0 | 0.041 |
| 2.0 | 0.078 |
| 1.0 | 0.140 |
| 0.5 | 0.254 |
| None | 0.773 |

At concentrations of 5.0 and 10.0 ug per ml of MAb H-5 the absorbance of the EIA was reduced by 94% or more.

C. BLOCKING OF UNIQUE EPITOPE

The blocking experiment was repeated using rabbit antisera which reacted with the unique LPS epitope of *C. trachomatis*. As in the previous experiment blocking antibody (MAb H 5) at various concentrations was added to the rabbit detector antibody used in the EIA. An unblocked control was included in the test. The LGV was tested at a concentration of 1.6 ×10$^4$ cells per ml. At a final concentration of 0.5 ug per ml the MAb blocked the absorbance of the EIA by 54%. At concentration of 5.0 and 10.0 ug per ml the absorbance was decreased by 91 and 95%, respectively (Table 3).

TABLE 3

| Final Concentration of MAb Added to Rabbit Antibody Solution | Net OD in EIA |
|---|---|
| 10.0 | 0.048 |
| 5.0 | 0.085 |
| 2.0 | 0.188 |
| 1.0 | 0.309 |
| 0.5 | 0.440 |
| None | 0.962 |

EXAMPLE 6

BLOCKING OF THE CHLAMYDIAZYME ® ASSAY WITH CBPs

A. MOUSE MABS CBPS

The mouse MAbs of Examples 2 and 4 were tested for blocking of the reaction of Chlamydiazyme ® reagent with an *Acinetobacter* strain, *S. minnesota* Re 595 and LGV strain 434. In a 1/500 dilution of ascites fluid, mouse MAbs H-5, H-69, H-35 and H210 each blocked the Chlamydiazyme ® reagent reaction with LGV. The reaction with two cross-reactive, gram negative bacteria, *Acinetobacter* and *S. minnesota* Re 595, was not blocked. The results are presented in Table 4.

TABLE 4

| MAb Added to Rabbit Anti-Chlamydia Reagent of Chlamydiazyme ® Kit | Absorbance in EIA with Various Test Antigens | | |
|---|---|---|---|
| | Acinetobacter | Salmonella Re 595 | LGV |
| None | 0.31 | 0.51 | 0.92 |
| H-5 | 0.34 | 0.47 | 0.01 |
| H-69 | 0.35 | 0.47 | 0.09 |
| H-35 | 0.32 | 0.43 | 0.32 |
| H-210 | 0.37 | 0.53 | 0.19 |

B. RAT MAB CBP

The rat MAb H-98 blocked the reaction of Chlamydiazyme ® reagent with LGV but did not block the reaction with *Acinetobacter* and *Salmonella* Re 595. The rat Mab was tested as a 1/10 dilution of tissue culture fluid in which the rat hybridoma was grown. The results are presented in Table 5.

TABLE 5

| MAb Added to Rabbit Anti-Chlamydia Reagent of Chlamydiazyme ® Kit | Absorbance in EIA with Various Test Antigens | | |
|---|---|---|---|
| | Acinetobacter | Salmonella Re 595 | LGV |
| None | 0.24 | 0.41 | 0.83 |
| H-98 | 0.26 | 0.38 | 0.26 |

C. POLYCLONAL CBP

The confirmatory assay can be performed using polyclonal antisera as the CBP reagent to block the binding of Chlamydiazyme ® DBP. If polyclonal antisera is used, the antisera must have reactivity with the unique chlamydial LPS epitope. Reactivity to the cross-reactive epitope must not be present in the antisera. If present, cross-reactive antibody can be removed by adsorption with *Salmonella* Re 595 as described in Example 5. Polyclonal antisera produced by immunization of guinea pigs with LGV strain 434 mixed with Freund's complete adjuvant is suitable as a CBP reagent. The antisera is used at a 1/500 dilution, or at a strength comparable to that of the CBP reagents of parts A and B above.

What is claimed is:

1. A method of confirming the presence in a sample of a *Chlamydia* antigen, the method comprising:
   (a) contacting a sample with a detector binding agent (DBP) capable of binding to a first site of a *Chlamydia* antigen to give a first measurable signal;
   (b) contacting a second confirmatory sample with reagent means comprising a confirmatory binding agent (CBP) capable of binding a second site of said antigen, said binding to the second site preventing binding of the DBP to the first site;
   (c) similarly contacting the second confirmatory sample with reagent means containing DBP capable of generating a signal;
   (d) separating DBP bound to sample antigen from unbound DBP in the second confirmatory sample; and
   (e) measuring a second signal from said second confirmatory sample of bound DBP, whereby a predetermined decrease in signal from sample-bound DBP relative to the first signal confirms the presence of the antigen in the sample.

2. The method according to claim 1 wherein the CBP, when bound to the second site, prevents the binding of the DBP to the first site by steric hindrance.

3. The method according to claim 1 wherein the CBP comprises an antibody.

4. The method according to claim 1 wherein the CBP comprise a monoclonal antibody.

5. The method according to claim 1 wherein the contacting steps b) and c) are performed simultaneously.

6. The method according to claim 5 wherein the reagent means containing the CBP and the reagent means containing the DBP are mixed together prior to contacting the sample.

7. The method according to claim 1 wherein the first and second sites are adjacent or overlapping sites on the *Chlamydia* lipopolysaccharide.

8. The method according to claim 1 wherein the antigen to be assayed is from the species *Chlamydia trachomatis*.

9. A method of confirming the presence in a sample of *Chlamydia* having a lipopolysaccharide (LPS) component of its cell membrane, the presence being detected in the potential presence of cross reactive organisms, said method comprising:
   (a) contacting a first sample with a detector binding agent (DBP) binding to a first antigenic epitope on the LPS to give a first measurable signal;
   (b) contacting a second confirmatory sample with reagent means comprising a confirmatory binding agent (CBP) capable of binding a second epitope on the LPS, said binding to the second epitope preventing binding of the DBP to the first epitope;
   (c) similarly contacting the second confirmatory sample with reagent means containing DBP capable of generating a signal;
   (d) separating DBP bound to sample antigen from unbound DBP in the second confirmatory sample; and
   (e) measuring a second signal from said second confirmatory sample of bound DBP, whereby a predetermined decrease in signal from sample-bound DBP relative to the first measurable signal confirms the presence of *Chlamydia* in the sample.

10. The method according to claim 9 wherein the CBP, when bound to the second epitope, prevents the binding of DBP to the first epitope by steric hindrance.

11. The method according to claim 9 wherein the CBP comprises a monoclonal antibody.

12. The method according to claim 9 wherein the contacting steps b) and c) are performed simultaneously.

13. The method according to claim 12 wherein the reagent means containing the CBP and the reagent means containing the DBP are mixed together prior to contacting the sample.

14. The method according to claim 9 wherein the first and second epitopes are adjacent or overlapping sites on the LPS.

15. The method according to claim 9 wherein the species whose presence is to be confirmed is trachomatis species.

* * * * *

UNITED STATES PATENT AND TRADEMARK OFFICE
CERTIFICATE OF CORRECTION

PATENT NO. : 5,064,755
DATED : November 12, 1991
INVENTOR(S) : Lawrence V. Howard, Jr. and MaryCaren Craine It is certified that error appears in the above-identified patent and that said Letters Patent is hereby corrected as shown below:

Column 9, line 16: "similarly" should be deleted.

Column 10, line 10: "capable of" should be inserted after "(DBP)" and before the word "binding".

Column 10, line 17: "similarly" should be deleted.

Column 10, line 44: Change the word "species" to "Chlamydia".

Column 10, line 44: Insert the word "Chlamydia" before the word "trachomatis".

Signed and Sealed this

Ninth Day of July, 1996

Attest:

BRUCE LEHMAN

Attesting Officer

Commissioner of Patents and Trademarks